United States Patent [19]

Natori

[11] Patent Number: 5,196,303

[45] Date of Patent: Mar. 23, 1993

[54] CLONING OF DNA ENCODING TRANSCRIPTION FACTOR S-II AND UTILIZATION OF THE DNA

[75] Inventor: Shunji Natori, Tone, Japan

[73] Assignee: Sanwa Kagaku Kenkyusho Co., Ltd., Nagoya, Japan

[21] Appl. No.: 683,922

[22] Filed: Apr. 11, 1991

Related U.S. Application Data

[62] Division of Ser. No. 246,244, Sep. 19, 1988, Pat. No. 5,055,392.

[30] Foreign Application Priority Data

Sep. 29, 1987 [JP] Japan .................... 62-242817

[51] Int. Cl.[5] .................... C12Q 1/68; C12Q 1/70; C12N 15/00; C07H 15/12
[52] U.S. Cl. .................... 435/5; 435/6; 435/172.3; 435/320.1; 536/27
[58] Field of Search .................... 435/6, 520, 172.3, 5, 435/320.1; 536/27

[56] References Cited

U.S. PATENT DOCUMENTS 5,055,392 11/1991 Natori et al. .................... 435/6

OTHER PUBLICATIONS

Itirai et al. Bioch. et Biphys. Act. 868:243 (1986).
Hirashima et al. J. of Biol. Chem 263(8):3858 (1988).
Reinberg et al. J. of Biol Chem. 262(7) 3331 (1987).
Suggs et al. P.N.A.S. 78(11):6613 (1981).

*Primary Examiner*—Robert A. Wax
*Assistant Examiner*—Miguel H. Escallon
*Attorney, Agent, or Firm*—Nikaido, Marmelstein, Murray & Oram

[57] ABSTRACT

A cloned single-strand DNA encoding amino acid sequence for a eukaryotic transcription factor S-II is disclosed together with, a cloned double-strand DNA consisting of the single-strand DNA and its complementary single-strand DNA, a DNA fragment of the single- or double-strand DNA, a process for the preparation thereof, a plasmid, in which the double-strand DNA or its fragment is inserted, and a diagnosis of viral diseases and cancers.

1 Claim, 8 Drawing Sheets

E: EcoRI     D: DraI
X: XhoI      Pv: PvuII
P: PstI      B: BamHI
S: SacI      H: HindIII

FIG. 2

Peak I :
```
           1                       5
         Asp Thr Tyr Val Ser Ser Phe Pro Arg
```

Peak II :
```
           1                            10
         Thr Gly Asp Asp Tyr Val Ala Ile Gly Ala Asp Glu Glu Leu Gly
                           A
         3'-CTA CTA ATA CAG CG-5'    3'-CTA CTC CTC CTC AA-5'
                G   G   G   C                G   T   T   G
                            T
```

FIG. 4(a)

```
▶pSII-1       ▶pSII-3
1
GAATTCGGACACAGCGGAAGCGGACAGAGAAGCTGCGCGACGTTGGACACAGCCGCGAACGCGCTGGCCGAGGCCTTCCGGAGCCATG
                    20                  40                  60                  80    Met  1
                                                                   (1)
                                                             pSII-2 ▶GA

GAGGACGAGGTGGTTCGCATTGCCAAGAAGATGACAAAAATGGTGCAGAAAAAGAATGCGGTGGCCGCATTGATTTGCTGAAAGAG
            100                 120                 140                 160
GluAspGluValValArgIleAlaLysLysMetAspLysMetValGlnLysLysAsnAlaGlyAlaAlaLeuAspLeuLeuLysLysGlu  30
```

FIG. 4(b)

```
        180            200            220            240            260
CTTAAGAATATTCCCATGACCCTAGAATTGCTACAGTCCACAGTGGAATGTCTGTCAATGCCCTTCGCAAGCAGAGCACAGAT    59
LeuLysAsnIleProMetThrLeuGluLeuLeuGlnSerThrArgIleGlyMetSerValAlaLeuArgLysGlnSerThrAsp 280            300            320            340
GAAGAAGTCACCTCTCTAGCCAAGTCTCTCATCAAATCCTGGAAAAAATTATTAGATGGACCATCAACTGATAAAGACCCTGAAGAA    88
GluGluValThrSerLeuAlaLysSerLeuIleLysSerTrpLysLysLeuLeuAspGlyProSerThrAspLysAspProGluGlu 360            380            400            420
AAGAAAAAGAGCCTGCAATTTCATCACAGAATAGCCCTGAAGCAAGAAAGTAGTTCCAGCAGCAATGTAAGCAGCAGAAAG          117
LysLysLysGluProAlaIleSerSerGlnAsnSerProGluAlaArgGluSerSerSerSerAsnValSerSerArgLys 440            460            480            500            520
GATGAGACAAATGCTCGAGATACATAGTTCATCTTTCCTCGCGCACCAAGCACTTCTGATTCTGTGCGATTAAAAATGTAGGGAG    146
AspGluThrAsnAlaArgAspThrTyrValSerSerPheProArgAlaProSerThrSerAspSerValArgLeuLysCysArgGlu 540            560            580            600
ATGCTTGCTGCAGCTCTTCCGGACAGGAGATGATTATGTTGCAATTGGAGCTGATGAAGAAGAACTGGGATCTCAGATTGAGGAAGCT    175
MetLeuAlaAlaAlaLeuArgThrGlyAspTyrValAlaIleGlyLeuLeuAlaAspGluGluLeuGlyLeuGlySerGlnIleGluGluAla 620            640            660            680
ATATATCAAGAAATAAGGAATACAGACATGAAATACAAAAACAGAGTACGAAGTAGGATACATCAAATCTTAAAGATGCAAAGAATCCA    204
IleTyrGlnGluIleArgAsnThrAspMetLysTyrLysAsnArgValArgSerArgIleSerAsnLeuLysAspAlaLysAsnPro
```

FIG. 4(c)

```
700                    720                    740                    760                    780
AATTTAAGGAAAAATGTGCTGTGTGGGAATATTCCTCCTGATCTATTTGCTAGAATGACAGCAGAGGAAATGGCTAGTGATGAGCTC     233
AsnLeuArgLysAsnValLeuCysGlyAsnIleProProAspLeuPheAlaArgMetThrAlaGluMetAlaSerAspGluLeu
                                  pS II-1

800                    820                    840                    860
AAAGAGATGAGGAAAAACCTGACCAAAGAAGCCATCAGGGACCCAAGACTGGTGGGACCCAGACTGACTTGTTCACT                 262
LysGluMetArgLysAsnLeuThrLysGluAlaIleArgHisGlnMetAlaLysThrGlyGlyThrGlnThrAspLeuPheThr 880                    900                    920                    940
TGTGGCAAATGTAAAAGAAGAACTGCACTTATACACAGGTGCAAACTGTAGTGCTGATGAACCAATGACAACATTTGTGTA           290
CysGlyLysCysLysLysAsnCysThrTyrThrGlnValGlnThrArgSerAlaAspGluProMetThrThrPheValVal 960                    980                    1000                   1020                   1040
TGTAATGAATGTGAAATCGGGTGGAAGTTCTGTGAGTTTGGAAGAATTGGCAAGTATCTGGACCATTAAGAAAAAACTTAATTTG       301
CysAsnGluCysGlyAsnArgTrpLysPheCys***

1060                   1080                   1100                   1120
TTAATTAGCTTTAAAATTAAGCCAGGCAACTCGTTCCTTGCAAGTGAAATTGTAAACAACATACATCTCATGGGTGGTCTTTGT 1140                   1160                   1180                   1200
TGTTCACCTGACAGTCTGTCTTAAATGCCTTCTGTGGTCTCAGATCAGCTGGGAGACCATAAAATAATGATATAATGTGTTGCTTTG
                                                                            pS II-3
```

FIG. 4(d)

```
1220                1240                1260                1280                1300
TTTTCTCTTCATAAGTTGATGTTGCATTTTATTAAATATTAACTTTTTATAGCCTAGAACACAAAAATTTGTTGATCTGTTAATGCA 1320                1340                1360                1380
TAAAGATAAATTGCTTTCTCATTGGTATGTACCTAAACATGTTAAAGGAAAAGGCATAATATAAATTTTAGAGTTACCAAATGTAGT 1400                1420                1440                1460                1480
GTGTATTCCAATAGTATGTGGCCAGCTTATCAAAGTTGTGCACACAATTTGAACTAGCATATTACTTTACTCTTAATTACTGTGCTCACA 1520                1540                1560
AAGCCTCGGATCCTTGGATCTCTTGCATCTGTGACTAACCACAGTGATCATTTCTTTTATTCTCATACATATAATACCATTTTTAA 1580                1600                1620                1640                1660
TAGATTTTACTCTGAAAACGGACTTGGTTTATTTGACTTTGTGCTATATTTAGTTTTATAGAACTCTGTTATAATTCCTAAGC 1680                1700                1720                1740
TTTTCATAAAGCCCACCACAGGTATACTTCTGATGAATTGTCCCCAATAGGAAGACATGCTATGAAGAAAATGTTAGTATCTTAGTAGAC 1760                1780                1800                1820                1840
TTCCTGGAGGCAGCATGACTGTACTTGCACTTGGAAAACCTACTGACCAAGGATTAAGCCTGAGAACTGTAAATCATTAAGCTATGCTC 1880                1900                1920
TTTGTGTATGGAGGTTGCAAAAAAGGCACCTCCCTTAGACTGAATCTTTGTGCTGAAATTTTCTTACATGATGTGTCAACCCAGCT
```

FIG. 4(e)

```
1940                      1960                      1980                      2000                      2020
GAAATGTAGGCTGTAGCAAATAGTTTACAAAACATATTTCACAATATTTCACTTTTAAATGTGTCCCACTTGTTTTGCTAGTAAT 2040                      2060                      2080                      2100
AAGCAGTGGTTTCACATCGTCTTCCTGAGAGAGATGTGTAATGCATATAGTAAAGGCCACTTTTATAAATTAAGTGCTTCTGCCTGTG 2120                      2140                      2160                      2180                      2200
TTCAGACTCCCTGTGTAAAAACCGTTGCACAAGCTTTGCACTCTTCTATGCTCTGCTTTGTAGACCGTTGTCATAACATGAAAACAATA 2220                      2240                      2260                      2280
TGTCCAATGTAAAAGGATTGGTCTGCCGGGGTGGTGGCCCACACCTTTAATCCCAGAACTCGGGAGGCAGAGGCGGATTTCTGAG 2300                      2320                      2340                      2360                      2380
TTTGAGGGCCAGCCTGGTCTACAGAGTGAGTTCCAGGACAGCCAGGGCTATACAGAGAAACCCTGTCTCAACCCCCTCCCCCCCAAAA 2400                      2420                      2440                      2460
AAAAGATTGGTCCATGGATAATTTCGTCACTTTAAAAATAAAGTACAGTTTGAAAGAATTAGTTTAAAGTAATAAGGTTAAAATAGTC 2480                      2500                      2520                      2535
CCACTTTAAGTGATCCATTTTAAAATTTGTAAATCAATAAAGTTTTTTGTTGTTAAAC - - - - poly A
pSII-2↑
```

1

CLONING OF DNA ENCODING TRANSCRIPTION FACTOR S-II AND UTILIZATION OF THE DNA

This is a division of application Ser. No. 246,244, filed Sep. 19, 1988, now U.S. Pat. No. 5,055,392.

BACKGROUND OF THE INVENTION

1. Field of the Invention

The present invention relates to a cloned single-strand DNA encoding amino acid sequence for a eukaryotic transcription factor S-II, a cloned double-strand DNA consisting of the single-strand DNA and its complementary single-strand DNA, a DNA fragment of the single- or double-strand DNA, a process for the preparation thereof, a plasmid, in which the double-strand DNA or its fragment is inserted, and a diagnostic reagent for the detection of diseases and more particularly viral diseases and cancers.

2. Related Arts

A transcription factor S-II is a protein, which was first separated and isolated by the present inventor from an Ehrlich ascites tumor cell and which shows a promotion of accuracy and efficiency of transcription through an eukaryotic RNA polymerase II ["Mol. Cell. Biochem." Vol. 46, pages 173-187 (1982)]. Thereafter, the same transcription factor has also been isolated from a bovine thymus suggesting that the substance is the factor commonly presents in eukaryotic cells ["J. Biol. Chem." Vol. 262, pages 5227-5232 (1987)].

In connection with a diagnosis of viral diseases and cancers, and more particularly the acquired immune deficiency syndrome (AIDS) among the virus diseases, a diagnosis using an antibody to HIV has generally been employed. Retroviruses such as HIV has been known to replicate using host RNA polymerase II. Besides RNA polymerase II, it is widely acknowledged that various cellular factors play a roll in eukaryotic transcriptional controls.

It has been apparent, as referred to, that the transcription factor S-II is present in eukaryotic cells, but its structure has not been elucidated. According to the prior arts, further, the transcription factor S-II has been prepared by separation and extraction from the cells and thus the preparation thereof in large amount was difficult.

While, various methods have been proposed to use a certain antibody for making a diagnosis of viral diseases and cancers and, more particularly, in the diagnosis of AIDS, such an antibody diagnosis is not always conclusive and there is no subsidiary diagnostic method, which sometimes makes impossible rather than difficult an exact diagnosis, such as when an antigen-antibody reaction shows a false positive.

SUMMARY OF THE INVENTION

A basic object of the invention, therefore, is to develop a process for large scale preparation of the transcription factor S-II by utilizing so-called "Bio-Technology" and a diagnostic method for viral diseases and cancers, which utilizes a gene of the transcription factor S-II.

A primary object of the invention, therefore, is to provide a cloned DNA comprising the transcription factor S-II and a fragment of the DNA to allow a large scale preparation of the transcription factor S-II by use of a recombinant DNA methods.

An additional object of the invention is to provide the diagnostic method for AIDS and other viral diseases and cancers, which employs a cloned DNA comprising the transcription factor S-II or the DNA fragment, so as to increase diagnostic accuracy for the diseases by combining the method with any one of known conventional methods.

The present inventor has carefully and energetically studied and investigated the problem to finally gain success of cloning in the DNA in the region containing the transcription factor S-II to determine its structure and to find out that in cancer cells and cells infected by virus, and more particularly cells infected with HIV, an expression of mRNA for transcription factor S-II becomes augmentative, for instance 10 fold or more, in comparison with that in normal cells.

DETAILED DESCRIPTION OF THE INVENTION

According to the invention, the primary object can be attained using isolated cloned single-strand DNA comprising about 2500 nucleotides which contains a nucleotide sequence encoding an amino acid sequence for the eukaryotic transcription factor S-II, or a cloned double-strand DNA consisting of the single-strand DNA and its complementary single-strand DNA.

According to a process of the invention, the cloned single- or double-strand DNA can be prepared by extraction and purification of poly(A)RNA from Ehrlich ascites tumor cells, constructing a cDNA library with use of the poly(A)RNA and a vector DNA to carry out a transformation of *Escherichia coli* (*E. coli*), while, previously synthesizing a mixture of 32 dotriacontamers, each consisting of 14 oligodeoxyribonucleotides of the formula

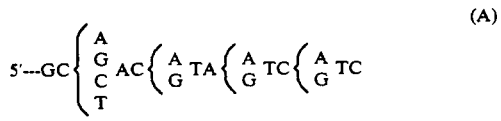  (A)

which is complementary to mRNA corresponding to

Asp—Asp—Tyr—Val—Ala of 3rd to 7th amino acids from N-terminal in known amino acid sequence in peak II for a fragment which is obtained by cleaving with trypsin the known transcription factor S-II obtained from Ehrlich ascites tumor cells and a mixture of 32 dotriacontamers, each consisting of 14 oligodeoxyribonucleotides of the formula

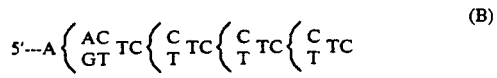  (B)

which is complementary to mRNA corresponding to

Asp—Glu—Glu—Glu—Leu of 11th to 15th amino acids from N-terminal in the known amino acid sequence, labelling each synthesized oligodeoxyribonucleotides shown by said formulae (A) and (B) at its N-terminus, screening said transformed *E. coli* by hybridization using said labelled oligodeoxyribonucleotides as probes to obtain a cloned double-strand DNA as positive clone which hybridizes to both of the probe groups, and if necessary, separating the double-strand DNA into single-strand DNA, in a conventional manner.

The ground that the 3rd to 7th amino acids from N-terminal in amino acid sequence of the known polypeptide for transcription factor S-II are selected for the oligodeoxyribonucleotides (A) as one of probe groups and that the 11th to 15th amino acids from N-terminal amino acid sequence of the known polypeptide for transcription factor S-II are selected for the oligodeoxyribonucleotides (B) as the other probe group lies in minimizing the kinds of oligodeoxyribonucleotides to be synthesized for responding to the pentapeptide. In the screening of the transformed cells (*E. coli*), there is no difference in result, even if the hybridization with the oligodeoxyribonucleotides (A) is carried out prior to that with the other oligodeoxyribonucleotides (B), or vice versa. The cloned single-strand DNA can be prepared by separating the cloned double-strand DNA with use of a method known per se, for instance thermally treating at 90° C. for about 3 minutes and then cooling the same with use of an ice bath.

The transcription factor S-II according to the invention has about 900 nucleotides of the following nucleotide sequence or any other nucleotide sequence producing the same protein, taking into consideration the redundancy of the genetic code.

```
5'— ATG GAG GAC GAG GTG GTT CGC ATT GCC AAG AAG ATG GAC AAA ATG
    GTG CAG AAA AAG AAT GCG GCT GGC GCA TTG GAT TTG CTG AAA GAG
    CTT AAG AAT ATT CCC ATG ACC CTA GAA TTG CTA CAG TCC ACA AGA
    ATT GGA ATG TCT GTC AAT GCC CTT CGC AAG CAC AGC ACA GAT GAA
    GAA GTC ACC TCT CTA GCC AAG TCT CTC ATC AAA TCC TGG AAA AAA
    TTA TTA GAT GGA CCA TCA ACT GAT AAA GAC CCT GAA GAA AAG AAA
    AAA GAG CCT GCA ATT TCA TCA CAG AAT AGC CCT GAA GCA AGA GAA
    GAA AGT AGT TCC AGC AGC AAT GTA AGC AGC AGA AAG GAT GAC ACA
    AAT GCT CGA GAT ACA TAT GTT TCA TCT TTT CCT CGC GCA CCA AGC
    ACT TCT GAT TCT GTG CGA TTA AAA TGT AGG GAC ATG CTT GCT GCA
    GCT CTT CGC ACA GGA GAT TAT GTT GCA ATT GGA GCT GAT GAA
    GAA GAA CTG GGA TCT CAG ATT GAG GAA GCT ATA TAT CAA GAA ATA
    AGG AAT ACA GAC ATG AAA TAC AAA AAC AGA GTA CGA AGT AGG ATA
    TCA AAT CTT AAA GAT GCA AAG AAT CCA AAT TTA AGG AAA AAT GTG
    CTG TGT GGG AAT ATT CCT CCT GAT CTA TTT GCT AGA ATG ACA GCA
    GAG GAA ATG GCT AGT GAT GAG CTC AAA GAG ATG AGG AAA AAC CTG
    ACC AAA GAA GCC ATC AGG GAG CAT CAG ATG GCC AAG ACT GGT GGG
    ACC CAG ACT GAC TTG TTC ACT TGT GGC AAA TGT AAA AAG AAG AAC
    TGC ACT TAT ACA CAG GTG CAA ACT CGT AGT GCT GAT GAA CCA ATG
    ACA ACA TTT GTT GTA TGT AAT GAA TGT GGA AAT CGG TGG AAG TTC
    TGT —3'
``` wherein A, C, G and T are respectively an oligodeoxyribonucleotide having adenine, cytosine, guanine or thymine base and said sequence is given as that of each codon corresponding to a specified amino acid.

The term of --Nucleotide sequence producing the same protein means a case of that even when the arrangement of nucleotides constituting codons, such as --TTA-- and --CTG-- are different but each of the codons designates same amino acid, according to the redundancy of the genetic code. Therefore, the term means all known or possible nucleotide sequences encoding the following amino acid sequence:

Met—Glu—Asp—Glu—Val—Val—Arg—Ile—Ala—Lys—Lys—Met—Asp—Lys—Met—

Val—Gln—Lys—Lys—Asn—Ala—Gly—Ala—Ala—Leu—Asp—Leu—Leu—Lys—Glu—

Leu—Lys—Asn—Ile—Pro—Met—Thr—Leu—Glu—Leu—Leu—Gln—Ser—Thr—Arg—

Ile—Gly—Met—Ser—Val—Asn—Ala—Leu—Arg—Lys—Gln—Ser—Thr—Asp—Glu—

Glu—Val—Thr—Ser—Leu—Ala—Lys—Ser—Leu—Ile—Lys—Ser—Trp—Lys—Lys—

Leu—Leu—Asp—Gly—Pro—Ser—Thr—Asp—Lys—Asp—Pro—Glu—Glu—Lys—Lys—

Lys—Glu—Pro—Ala—Ile—Ser—Ser—Gln—Asn—Ser—Pro—Glu—Ala—Arg—Glu—

Glu—Ser—Ser—Ser—Ser—Ser—Asn—Val—Ser—Ser—Arg—Lys—Asp—Glu—Thr—

Asn—Ala—Arg—Asp—Thr—Tyr—Val—Ser—Ser—Phe—Pro—Arg—Ala—Pro—Ser—

Thr—Ser—Asp—Ser—Val—Arg—Leu—Lys—Cys—Arg—Glu—Met—Leu—Ala—Ala—

Ala—Leu—Arg—Thr—Gly—Asp—Asp—Tyr—Val—Ala—Ile—Gly—Ala—Asp—Glu—

Glu—Glu—Leu—Gly—Ser—Gln—Ile—Glu—Glu—Ala—Ile—Tyr—Gln—Glu—Ile—

Arg—Asn—Thr—Asp—Met—Lys—Tyr—Lys—Asn—Arg—Val—Arg—Ser—Arg—Ile—

Ser—Asn—Leu—Lys—Asp—Ala—Lys—Asn—Pro—Asn—Leu—Arg—Lys—Asn—Val—

Leu—Cys—Gly—Asn—Ile—Pro—Pro—Asp—Leu—Phe—Ala—Arg—Met—Thr—Ala—

Glu—Glu—Met—Ala—Ser—Asp—Glu—Leu—Lys—Glu—Met—Arg—Lys—Asn—Leu—

Thr—Lys—Glu—Ala—Ile—Arg—Glu—His—Gln—Met—Ala—Lys—Thr—Gly—Gly—

-continued

Thr—Gln—Thr—Asp—Leu—Phe—Thr—Cys—Gly—Lys—Cys—Lys—Lys—Lys—Asn—

Cys—Thr—Tyr—thr—Gln—Val—Gln—Thr—Arg—Ser—Ala—Asp—Glu—Pro—Met—

Thr—Thr—Phe—Val—Val—Cys—Asn—Glu—Cys—Gly—Asn—Arg—Trp—Lys—Phe—

Cys

The cloned DNA having about 900 nucleotides can be obtained by treating the cloned DNA having about 2500 nucleotides with a suitable restriction enzyme(s), for instance EcoRI and PvuII, and shorter fragments can be prepared by treating the cloned DNA having about 2500 to 900 nucleotides with a suitable restriction enzyme(s). In case of that a desired fragment can not be obtained with the treatment by the restriction envated the same, the transcription factor S-II or other biologically active substances can be produced in a large amount.

A diagnostic method for viral diseases and cancers according to the invention is characterized by labelling the cloned DNA having about 2500 nucleotides which include the nucleotide sequence encoding the amino acid sequence for the transcription factor S-II of Met—Glu—Asp—Glu—Val—Val—Arg—Ile—Ala—Lys—Lys—Met—Asp—Lys—Met—

Val—Gln—Lys—Lys—Asn—Ala—Gly—Ala—Ala—Leu—Asp—Leu—Leu—Lys—Glu—

Leu—Lys—Asn—Ile—Pro—Met—Thr—Leu—Glu—Leu—Leu—Gln—Ser—Thr—Arg—

Ile—Gly—Met—Ser—Val—Asn—Ala—Leu—Arg—Lys—Gln—Ser—Thr—Asp—Glu—

Glu—Val—Thr—Ser—Leu—Ala—Lys—Ser—Leu—Ile—Lys—Ser—Trp—Lys—Lys—

Leu—Leu—Asp—Gly—Pro—Ser—Thr—Asp—Lys—Asp—Pro—Glu—Glu—Lys—Lys—

Lys—Glu—Pro—Ala—Ile—Ser—Ser—Gln—Asn—Ser—Pro—Glu—Ala—Arg—Glu—

Glu—Ser—Ser—Ser—Ser—Ser—Asn—Val—Ser—Ser—Arg—Lys—Asp—Glu—Thr—

Asn—Ala—Arg—Asp—Thr—Tyr—Val—Ser—Ser—Phe—Pro—Arg—Ala—Pro—Ser—

Thr—Ser—Asp—Ser—Val—Arg—Leu—Lys—Cys—Arg—Glu—Met—Leu—Ala—Ala—

Ala—Leu—Arg—Thr—Gly—Asp—Asp—Tyr—Val—Ala—Ile—Gly—Ala—Asp—Glu—

Glu—Glu—Leu—Gly—Ser—Gln—Ile—Glu—Glu—Ala—Ile—Tyr—Gln—Glu—Ile—

Arg—Asn—Thr—Asp—Met—Lys—Tyr—Lys—Asn—Arg—Val—Arg—Ser—Arg—Ile—

Ser—Asn—Leu—Lys—Asp—Ala—Lys—Asn—Pro—Asn—Leu—Arg—Lys—Asn—Val—

Leu—Cys—Gly—Asn—Ile—Pro—Pro—Asp—Leu—Phe—Ala—Arg—Met—Thr—Ala—

Glu—Glu—Met—Ala—Ser—Asp—Glu—Leu—Lys—Glu—Met—Arg—Lys—Asn—Leu—

Thr—Lys—Glu—Ala—Ile—Arg—Glu—His—Gln—Met—Ala—Lys—Thr—Gly—Gly—

Thr—Gln—Thr—Asp—Leu—Phe—Thr—Cys—Gly—Lys—Cys—Lys—Lys—Lys—Asn—

Cys—Thr—Tyr—thr—Gln—Val—Gln—Thr—Arg—Ser—Ala—Asp—Glu—Pro—Met—

Thr—Thr—Phe—Val—Val—Cys—Asn—Glu—Cys—Gly—Asn—Arg—Trp—Lys—Phe—

Cys zyme(s), a region(s) not obtaining with the cleaving technique may be synthesized with use of a DNA synthesizer and the resulting region is(are) joined to one or both ends of the fragment obtained through the enzyme treatment.

The cloned DNA having about 2500 nucleotides, or any fragment thereof can be inserted into a plasmid with a technique known per se, for instance taking out a plasmid from E. coli, purifying the plasmid, treating the plasmid with a restriction enzyme(s) to cleave the plasmid at the nucleotide position inherent in the enzyme, and ligating with a DNA ligase the cloned DNA to the cleavages of the cut plasmid to reconstruct a plasmid with the recombinant DNA.

If a microorganism or eukaryotic cell (L, CHO or the like) is transformed with the plasmid which contains the recombinant DNA according to the invention and cultior a fragment of the DNA, with a radioisotope to make the cloned DNA into a detectable probe, and dot-blot hybridizing between the probe and variously diluted samples of sample cytoplasmic fraction to quantitatively determine an expression of mRNA. Namely, the diagnostic method of the invention utilizes a finding that the gene expression of transcription factor S-II is different between normal cells and infected cells and that amount thereof on the latter cells shows 10 fold or more value of that on the former cells. When the cloned DNA fragment is employed for the genic diagnosis, the fragment should have a length of about 250 bp or more. The fragment is made into the probe by separating into single-strand DNA and labelled with the radioisotope.

BRIEF DESCRIPTION OF THE DRAWINGS

FIG. 2 shows amino acid sequences determined on peaks I and II in FIG. 1 as well as nucleotide sequences of probes employed for the determination;

FIGS. 4a-4e show a determined nucleotide sequence in the cloned DNA and an amino acid sequence forming an open reading frame therein;

PREFERRED EMBODIMENTS OF THE INVENTION

The invention will now be further explained with reference to Manufacturing Examples, Test Example for determining a structure of cloned DNA obtained by the Manufacturing Example and Diagnostic Example.

EXAMPLE 1

(a) Partial determination of amino acid sequence for transcription factor S-II

The transcription factor S-II (5 nmol) extracted and purified from Ehrlich ascites tumor cells and trypsin treated with tosylphenyalanylchloromethylketone were reacted in 1M-triethylamine/bicarbonate buffer solution and at 37° C. for 12 hours to obtain trypsin-treated fragment of the transcription factor S-II. The trypsin-treated fragment was chromatographed with use of a HPLC system mounted Synchropac RP-P(C-18). The conditions for the chromatography were a linear gradient of 5–60% acetonitrile in 0.05% trifluoroacetate and a flow velocity of 0.5 ml/min. Results are shown in FIG. 1.

Figure 1:
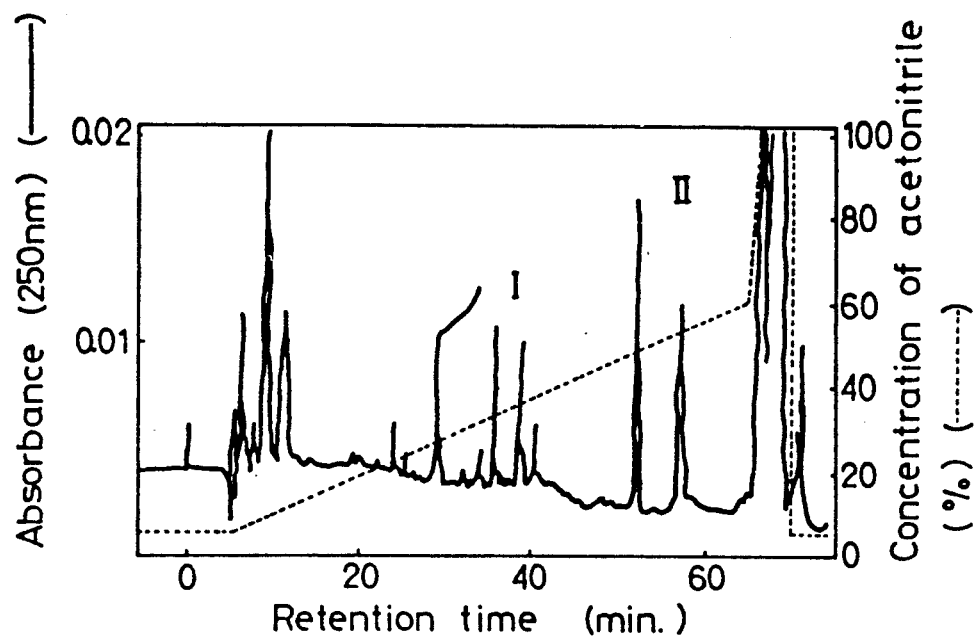
FIG. 1 shows HPLC pattern of the transcription factor S-II which was cleaved with trypsin.

Each of fractions I and II in FIG. 1 was obtained to determine an amino acid sequence with use of a protein sequencer (Type 470A, marketed by Applied Bio-System Corporation). Results are shown in FIG. 2. The Figure also shows nucleotide sequences of DNA employed as probes for determining the amino acid sequence on the peak II.

(b) Synthesis of DNA complementary to mRNA corresponding to amino acid sequence for transcription factor S-II A mixture of 32 dotriacontamers, each consisting of 14 oligodeoxyribonucleotides of the formula

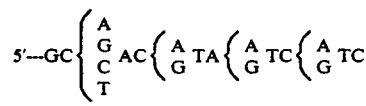

(A)

which is complementary to mRNA corresponding to

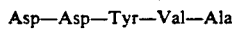

Asp—Asp—Tyr—Val—Ala of 3rd to 7th amino acids from the N-terminus in the amino acid sequence in peak II on the trypsin treated fragment, which amino acid sequence was elucidated by the method as disclosed in said Item (a) and a mixture of 32 dotriacontamers, each consisting of 14 oligodeoxyribonucleotides of the formula

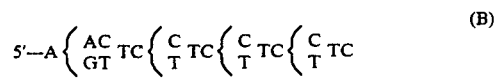

(B)

which is complementary to mRNA corresponding to

Asp—Glu—Glu—Glu—Leu of 11th to 15th amino acids from the N-terminus in the amino acid sequence were synthesized with use of a DNA synthesizer (Gene Assembler, marketed by Pharmacia AB). These synthetic nucleotides cover all possible cases for translating the amino acid sequence.

(c) Cloning

The cloning was carried out in accordance with the method as disclosed by Hanahan, D. et al ["Gene" Vol. 10, pages 63–67 (1980)].

Namely, a cDNA library was prepared with use of poly(A)RNA obtained from Ehrlich ascites tumor cells and a phage bector of λ gt10 and about 30000 transformed cells were taken out from the cDNA library. The transformants were replicated on a nitrocellulose filter. Plaques formed on the filter was fixed thereon with use of 0.5N-NaOH, neutralized to into pH into 7.5 and dipping the filter in 1.5M-NaCl containing Tris-chloride buffer (pH 7.5) to remove bacterial fragments and the like other than DNA. The filter was then air dried and baked for 2 hours at 80° C. to obtain a testing filter for screening, which carries the DNA of about 30000 transformants.

The screening of the transformants was carried out as follows, in accordance with the method as disclosed by Grunstein, M. et al ["Proc. Natl. Acad. Sci. U.S.A." Vol. 72, pages 3961–3965 (1975)].

Each of the oligodeoxyribonucleotides synthesized by the method as stated in said Item (b) and shown by said formula A was end-labelled at 5'-terminal with an radioisotope of [γ-$^{32}$P]ATP (marketed by Amersham, 5000 Ci/mmol) and T$_4$ polynucleotide kinase (marketed by Toyobo Co., Ltd., Osaka, Japan) to make the oligodeoxyribonucleotides into probes for screening of the transformants. The relative activity of each probe was 1 to 2×10$^6$ pm/pmol.

The transformants on the testing filter were screened by a hybridization at 20° C. and with use of the probes (A) and evaluated by an autoradiogram method to find that only 10 transformants among 3000 transformants are positive clones hybridizable with the probes (A).

These positive clones were further screened by another hybridization using the probes (B) which were synthesized as stated in Item (b) and labelled in a manner similar to the above, and judged as above to find that only one transformant is a positive clone hybridizable with the probes (B).

The clone hybridizable with origodeoxyribonucleotides (A) and (B) was analized by an electrophoresis to find that it has a cDNA insert region of about 800 bp. The cDNA insert region was sub-cloned into plasmid pUC8 to obtain a DNA recombinant plasmid which was named as --pS-II-1--(see FIG. 4).

To obtain a clone having more longer cDNA insert region, said cDNA insert region having about 800 bp was labelled by a radioisotope of $^{32}P$ by nick translation method to make it into a probe. Then, further screening was carried out with use of the probe on about 500000 transformants to obtain 7 positive clones. These positive clones were classified into two groups, one having a cDNA insert region of 2.6 kb and the other having a cDNA insert region of 1.3 kb. Each cDNA insert region was sub-cloned to plasmid pBSM13 to obtain a DNA recombinant plasmid which was named as --pSII-2-- and --pSII-3--, respectively (see FIG. 4).

Since each cDNA is double-strand and its nucleotide sequence has been elucidated as disclosed in the Test Example given later, it may be made into a fragment having various lengths in cDNA insert region, with use of a suitable restriction enzyme and a suitable synthetic DNA. These double-strand DNA or its fragments can be ligated into various plasmids, in accordance with conventional techniques, for instance by taking out a plasmid from E. coli, purifying same, treating the plasmid with a restriction enzyme to cleave the plasmid at a specified nucleotide position inherent to the restriction enzyme, and ligating with a DNA ligase the cloned DNA or its fragment to the cleavages of the cleaved plasmid to re-construct a plasmid with the recombinant DNA. A microorganism or eukaryotic cell can be transformed with such DNA recombinant plasmid in a conventional manner and cultivated to produce the transcription factor S-II or other specific biologically active substances, in a large amount.

TEST EXAMPLE

Determination of nucleotide sequence for cDNA including transcription factor S-II clone and amino acid sequence of the transcription factor S-II region A nucleotide sequence of cDNA clone encoding a transcription factor S-II was determined in accordance with the dideoxy method as disclosed by Sanger et al ["Proc. Natl. Acad. Sci. U.S.A." Vol. 74, pages 5463-5467 (1977)] and with use of the DNA recombinant plasmids, pS-II-1, pS-II-2 and pS-II-3 as disclosed in Item (c) of the Manufacturing Example 1.

Figure 3:
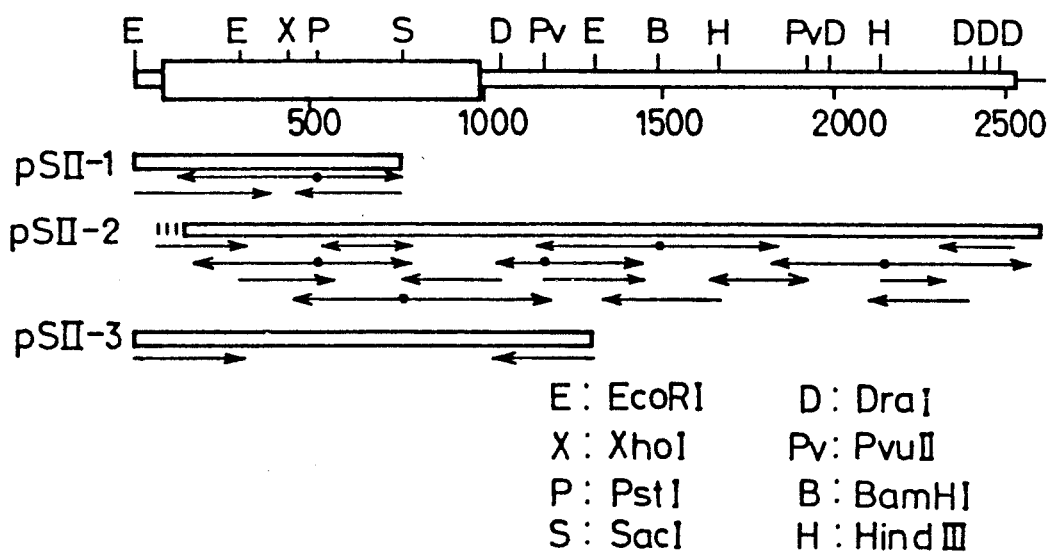
FIG. 3 shows a cloned DNA region including transcription factor S-II, restriction enzymes employed for determining nucleotide sequence in the region and a strategy for the determination of nucleotide sequence.

In FIG. 3, there are shown restriction enzymes employed for determining the nucleotide sequence and strategy for sequencing the cloned cDNA. In the Figure, symbols at uppermost portion are names of the selected restriction enzymes, in which X is XhoI, P PstI, S SacI, D DraI, Pv PvuII, B BamHI and H HindIII, respectively. A boxed region shows the region encoding the transcription factor S-II and upper and down stream regions are nontranslated flanking ones. The numerals at the middle portion are the nucleotide number. In the lowermost portion, horizontal arrows show a direction and range of the nucleotide sequence to be determined by the respective restriction enzyme.

Resulting nucleotide sequence of the transcription factor S-II clone is shown in FIG. 4 together with the corresponding amino acid sequence. In this Figure, numerals given at upper side of the nucleotide sequence are number of nucleotides as in FIG. 3, numerals given at right side of the amino acid sequence are the number of amino acid residues in the transcription factor S-II region, and the region boxed with a solid line shows that having the amino acid sequence overlap with a part of the amino acid sequence for transcription factor S-II, which was previously determined by the present inventor. The transcription factor S-II region lies as a long open reading frame biginning from the initiation codon of ATG and ending with the termination codon of TGA and includes nucleotide sequence encoding 301 amino acids. Near the 3'-end region, there is a nucleotide sequence of AATAA (positions in upper stream poly(A) sequence by 17 and 106 nucleotide residues) which is usually found in upper stream of poly(A) sequence in eukaryotic mRNA.

EXAMPLE 2

Figure 5:
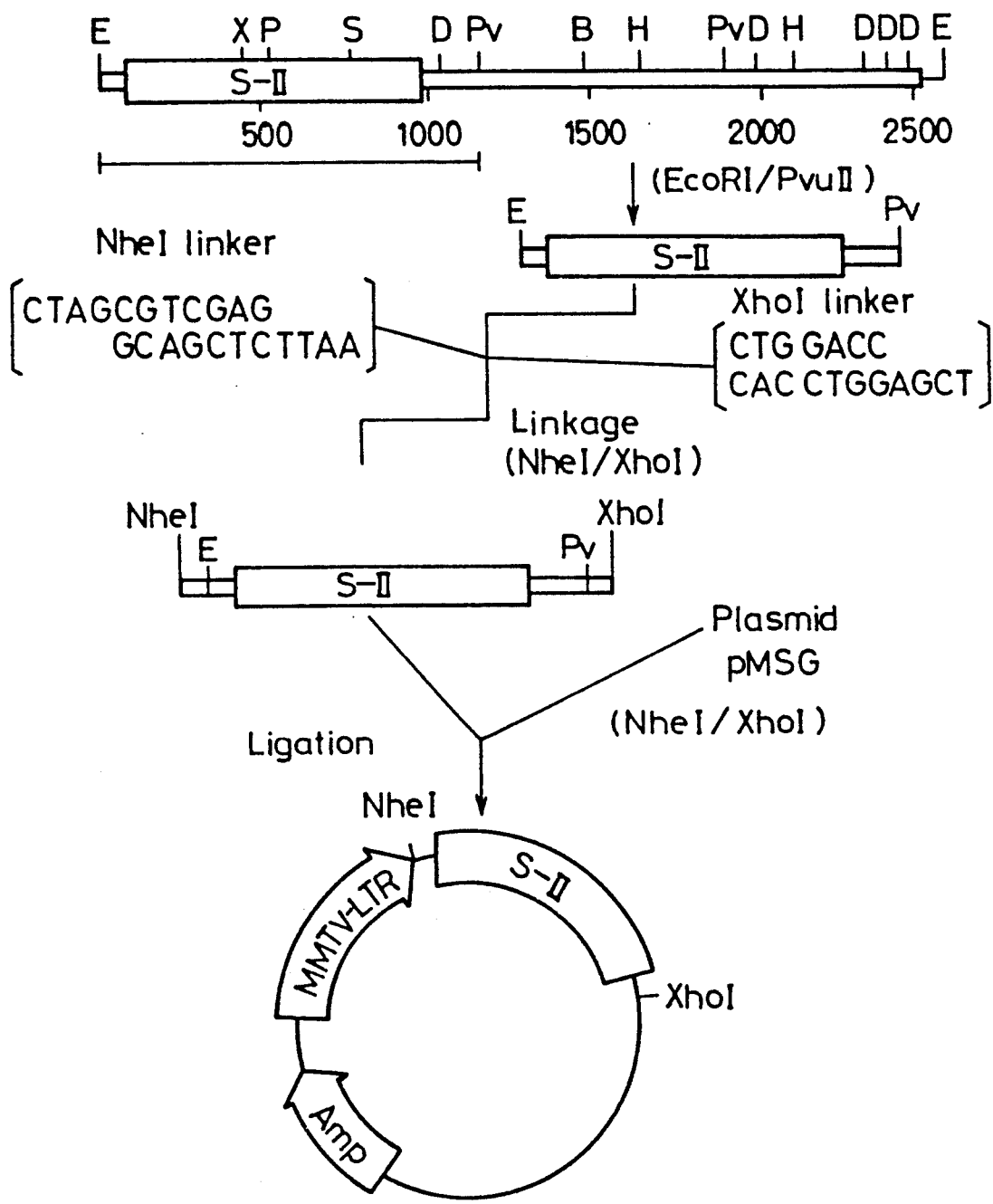
FIG. 5 illustrates steps for preparing a plasmid, wherein the transcription factor S-II is inserted.

Preparation of plasmid containing a cDNA clone encoding transcription factor S-II This embodiment will be explained with reference to the drawings and more particularly FIG. 5. First, the long DNA clone shown in FIGS. 3 and 4 was treated with restriction enzymes of EcoRI and PvuII to prepare a fragment of about 1100 bp. On the other hand, NheI and XhoI linkers as shown in FIG. 5 were prepared with use of a DNA synthesizer marketed by Pharmacia AB. These linkers were ligated to the EcoRI and PvuII sites, respectively.

A commercially available plasmid (pMSG) was treated with restriction enzymes of NheI and XhoI and said DNA encoding transcription factor S-II with the linkers was ligated with a DNA ligase to the cleavages of the plasmid to re-construct a desired plasmid. As shown at the last portion in FIG. 5, the resulting plasmid has the DNA clone of transcription factor S-II downstream of a powerful promoter (MMTV-LTR) which is long terminal repeat of mouse mammary tumor virus. The plasmid with such recombinant DNA can transform E. coli or the like, in a conventional manner, to produce the transcription factor S-II in a large amount.

DIAGNOSTIC TEST

Diagnosis of AIDS with use of cDNA clone for transcription factor S-II a) Preparation of probe The long DNA clone (single-strand DNA) for the transcriptional accelerator S-II and as shown in FIGS. 3 to 5 was treated with restriction enzymes EcoRI and PstI to prepare a fragment of about 600 bp. The fragment was labelled with radioisotope of $^{32}P$ by the nick translation method to make it into a probe.

b) Preparation of test samples

Cell strains of MoLT-4/III and Molt-4 were selected for the test, the former strain a source of HIV and the latter producing almost no HIV. Each of the strains was drown into an Eppendorf pipette ($10^6$ cells) and washed with 1 ml of phosphate buffer solution. In 45 µl of ice-cooled 10 mM-Tris chloride buffer containing 1 mM-EDTA, the cells were suspended and 5 µl of Nonidet P-40 (surface active agent marketed by Shell Chemicals Inc.) were added twice to the suspension in ice-bath for breaking the cells. The resulting solution was centrifuged (15000×g, 2.5 min.) to obtain a supernatant. The supernatant (50 µl) was collected into an Eppendorf tube, in which 30 µl of 20×NaCl/Cit (0.15M-NaCl/0.015M-sodium citrate) and 20 µl of 37(W/W) % formaldehyde solution had been previously added, to incubate at 60° C. for 15 minutes, so as to prepare an original sample solution. Preservation of the original sample solution shall be made at temperature of −70° C.

c) Preparation of testing filters

Each of original sample solutions was taken up in 20 μl, which was diluted with 15×NaCl/Cit in a serial system to prepare various test sample solutions, each having volume of 150 μl. Each diluted test sample solution was applied as 4 mm spots on a nitrocellulose sheet set on a 96 hole minifold marketed by Schleicher & Schuell GmbH and then the nitrocellulose sheet was baked at 80° C. for 3 hours to prepare a desired test filter.

d) Operation, results and consideration

A dot-blot hybridization was carried out with use of the probe stated in said Item a) and the test filter described therein item c) and the intensity of each spot was checked with an autoradiograph scanning to measure an expression of mRNA of transcription factor S-II.

Figure 6:
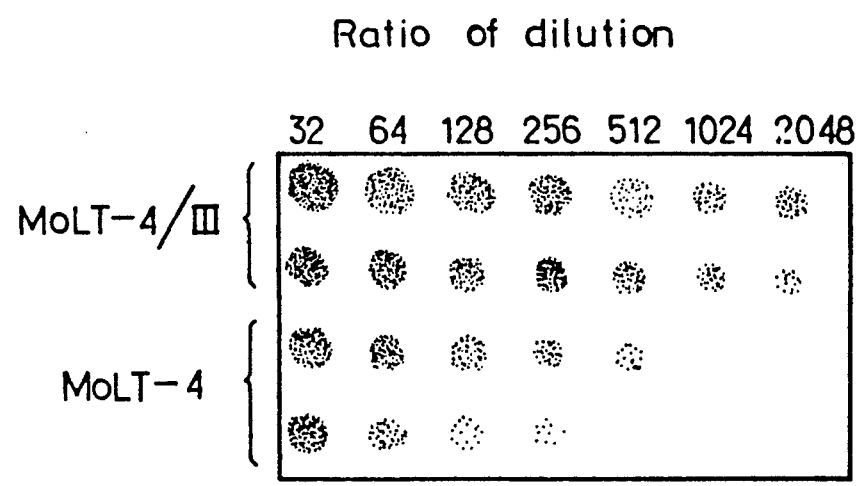
FIG. 6 shows results of diagnosis on AIDS, which was carried out by dot-blot hybridization method with use of the cloned DNA according to the invention.

Results are shown in FIG. 6. As apparently seen therefrom, a spot will not be recognized on the samples diluted 512 fold or more, in the MoLT-4 cells which discharge almost no AIDS virus. In the MoLT-4/III cells discharging HIV in a higher ratio, on the contrary thereto, a spot can be recognized, even when the sample was diluted by 2048 folds.

Therefore, if the operation as above will be carried out by selecting blood or the like cytoplasmic fraction, as an original sample, a diagnosis on AIDS is possible.

Further, an accuracy of the diagnosis on AIDS can remarkably be increased, when both of this genetic assay and a conventional antibody assay are carried out in combination.

What is claimed is:

1. A method for the diagnosis of HIV infection comprising steps of:
    a) preparing a probe by digesting a single-stranded DNA clone shown in FIG. 4 which encodes the transcriptional S-II of Ehrlich ascites tumor with restriction enzymes EcoRI and PstI to obtain a single-stranded DNA fragment with 534 deoxyribonucleotides, and labelling said fragment with a radioisotope;
    b) preparing a serial system of dilutions with a serum sample obtained from an individual to be diagnosed;
    c) preparing a test filter by spotting each diluted sample on a nitrocellulose filter and baking the same;
    d) carrying out a dot-blot hybridization with use of the probe and said test filter; and
    e) checking each spot with autoradiograph scanning to measure an expression of mRNA of transcriptional S-II.

* * * * *